United States Patent
Chen et al.

(10) Patent No.: US 9,896,433 B2
(45) Date of Patent: Feb. 20, 2018

(54) ANTIVIRAL COMPOUNDS

(71) Applicant: Hoffmann-La Roche Inc., Nutley, NJ (US)

(72) Inventors: Zhi Chen, Livingston, NJ (US); Elbert Chin, San Mateo, CA (US); Shawn David Erickson, Leonia, NJ (US); Stephen Deems Gabriel, Winterville, NC (US); Eric Mertz, Fair Lawn, NJ (US); Robert James Weikert, Clifton, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/766,646

(22) PCT Filed: Mar. 3, 2014

(86) PCT No.: PCT/EP2014/054032
§ 371 (c)(1),
(2) Date: Aug. 7, 2015

(87) PCT Pub. No.: WO2014/135483
PCT Pub. Date: Sep. 12, 2014

(65) Prior Publication Data
US 2015/0376165 A1  Dec. 31, 2015

Related U.S. Application Data

(60) Provisional application No. 61/772,919, filed on Mar. 5, 2013.

(51) Int. Cl.
| | | |
|---|---|---|
| C07D 251/48 | (2006.01) | |
| C07D 401/12 | (2006.01) | |
| C07D 403/12 | (2006.01) | |
| C07D 409/12 | (2006.01) | |
| C07D 417/12 | (2006.01) | |
| C07D 471/04 | (2006.01) | |
| A61K 31/4196 | (2006.01) | |
| A61K 31/427 | (2006.01) | |
| A61K 31/437 | (2006.01) | |
| A61K 31/4439 | (2006.01) | |
| A61K 31/501 | (2006.01) | |
| A61K 31/502 | (2006.01) | |
| A61K 38/21 | (2006.01) | |
| A61K 45/06 | (2006.01) | |

(52) U.S. Cl.
CPC ........ *C07D 401/12* (2013.01); *A61K 31/4196* (2013.01); *A61K 31/427* (2013.01); *A61K 31/437* (2013.01); *A61K 31/4439* (2013.01); *A61K 31/501* (2013.01); *A61K 31/502* (2013.01); *A61K 38/21* (2013.01); *A61K 45/06* (2013.01); *C07D 403/12* (2013.01); *C07D 409/12* (2013.01); *C07D 417/12* (2013.01); *C07D 471/04* (2013.01)

(58) Field of Classification Search
CPC ... C07D 251/48; C07D 401/12; C07D 409/12
See application file for complete search history.

(56) References Cited

U.S. PATENT DOCUMENTS

2004/0186288 A1    9/2004  Kruger et al.

FOREIGN PATENT DOCUMENTS

| WO | WO 2002064211 | * | 8/2002 |
| WO | WO2004046120 | * | 6/2004 |
| WO | 2013/103384 | | 7/2013 |
| WO | 2014006066 | | 1/2014 |

OTHER PUBLICATIONS http://www.cdc.gov/hepatitis/hcv/cfaq.htm, retrieved Aug. 15, 2016.*
Azev, 1993, Mendeleev Communications, vol. 3, No. 2, p. 49-50.*
Registry(STN) [online], Jun. 17, 2012 [Searched on Jul. 4, 2016], CAS Registry No. 1379353-14-6.
Registry(STN) [online], Mar. 26, 2004 [Searched on Jul. 4, 2016], CAS Registry No. 667866-13-9.
Registry(STN) [online], Mar. 26, 2004 [Searched on Jul. 4, 2016], CAS Registry No. 667865-33-0.
WO 02/094814, Nov. 2002, (An English language equivalent, US 20040186288, is citted).
The Japanese Office Action, dated Jul. 8, 2016, in the corresponding Japanese Application No. 2015-559518.
The Chinese Office Action, dated Aug. 18, 2016, in the corresponding Chinese Patent Appl. No. 201480011128.6.
The International Search Report and Written Opinion, dated Apr. 8, 2014, in the corresponding PCT Appl. No. PCT/EP2014/054032.

* cited by examiner

*Primary Examiner* — Michael Barker
*Assistant Examiner* — Karen Cheng

(57) ABSTRACT

The present invention discloses compounds of Formula I wherein the variables in Formula I are defined as described herein. Also disclosed are pharmaceutical compositions containing such compounds and methods for using the compounds of Formula I in the prevention or treatment of HCV infection.

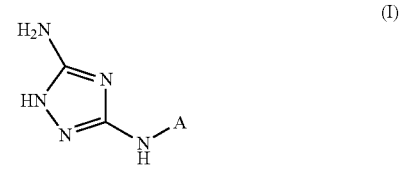

(I)

15 Claims, No Drawings

ANTIVIRAL COMPOUNDS

This application is a National Stage Application of PCT/EP2014/054032 filed Mar. 3, 2014, which claims priority from U.S. Provisional Patent Application No. 61/772,919, filed on Mar. 5, 2013. The priority of both said PCT and U.S. Provisional Patent Application are claimed.

The present invention provides compounds of Formula I useful as inhibitors of hepatitis C virus (HCV), as inhibitors of HCV infection, and for the prevention and treatment of hepatitis C infection.

Hepatitis C virus (HCV) infection is a major health problem that affects 170 million people worldwide and 3-4 million people in the United States (Armstrong, G. L., et al., Ann. Intern. Med. 2006, 144:705-714; Lauer, G. M., et al., N. Eng. J. Med. 2001, 345:41-52). HCV infection leads to chronic liver disease, such as cirrhosis and hepatocellular carcinoma in a substantial number of infected individuals. Chronic HCV infection associated liver cirrhosis and hepatocellular carcinoma are also the leading cause of liver transplantation in the United States. Current treatments for HCV infection include immunotherapy with pegylated interferon-α in combination with the nucleoside-analog ribavirin. Pegylated interferon-α in combination with ribavirin and one of the two recently approved HCV NS3 protease inhibitors Incivek or Victrelis is the current standard of care for the treatment of genotype 1 HCV infected patients, the most difficult to treat patient population. However, current HCV treatments are compromised by suboptimal sustained virological response rates and associated with severe side effects, as well as resistance to the protease inhibitors. Therefore there is a clear need for improved antiviral drugs with better efficacy, safety, and resistance profiles.

The infection of human hepatocytes by HCV, also known as HCV entry, is mediated by the functional interactions of virally-encoded envelope glycoproteins E1 and E2 and host cell co-receptors, followed by a receptor-mediated endocytosis processes. This HCV entry step is a putative target for therapeutic intervention. Several virally-encoded enzymes are also putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NSSB).

Systems have been developed to study the biology of HCV entry into host cells. Pseudotyping systems where the E1 and E2 glycoproteins are used to functionally replace the glycoproteins of retroviruses have been developed (Bartosch, B., Dubuisson, J. and Cosset, F.-L. J. Exp. Med. 2003, 197:633-642; Hsu, M. et al. Proc. Natl. Acad. Sci. USA. 2003, 100:7271-7276). These systems yield HCV pseudoparticles that bind to and enter host cells in a manner which is believed to be analogous to the natural virus, thus making them a convenient tool to study the viral entry steps as well as to identify inhibitors blocking this process.

There is a clear and long-felt need to develop effective therapeutics for treatment of HCV infection. Specifically, there is a need to develop compounds that selectively inhibit HCV viral entry and replication and that are useful for treating HCV-infected patients and protecting liver transplant patients from HCV re-infection. This application discloses novel compounds that are effective in prevention of HCV infection. Additionally, the disclosed compounds provide advantages for pharmaceutical uses, for example, with respect to their mechanism of action, binding, prevention of infection, inhibition efficacy, and target selectivity.

SUMMARY OF INVENTION

The application provides compound of formula I

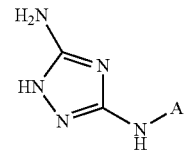

wherein:
A is unsaturated or partially saturated monocyclic or bicyclic heteroaryl, optionally substituted with one or more A'; and each A' is independently halo, halo lower alkyl, lower alkyl, or oxo;
or a pharmaceutically acceptable salt thereof.

The application provides a method for preventing a Hepatitis C Virus (HCV) infection comprising administering to a patient in need thereof a therapeutically effective amount of a compound of Formula I.

The application provides a method for treating a Hepatitis C Virus (HCV) infection comprising administering to a patient in need thereof a therapeutically effective amount of a compound of Formula I.

The application provides a composition comprising a compound of Formula I and a pharmaceutically acceptable excipient.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "••••••" drawn through a bond each refer to the point of attachment of a functional group or other chemical moiety to the rest of the molecule of which it is a part. Thus, for example:

MeC(=O)OR$^4$ wherein

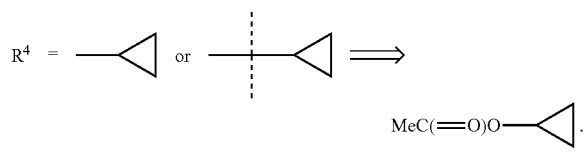

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

If a substituent is designated to be "absent", the substituent is not present.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "carbonyl" or "acyl" as used herein denotes a group of formula —C(=O)R wherein R is hydrogen or lower alkyl as defined herein.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "C$_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., (CH$_2$)$_n$) or a branched saturated divalent hydrocarbon radical of 2 to 10 carbon atoms (e.g., —CHMe— or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "haloalkoxy" or "halo lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The term "sulfinyl" as used herein denotes a —SO— group.

The term "sulfonyl" as used herein denotes a —SO$_2$— group.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The term "lower alkyl sulfonylamido" as used herein refers to a group of formula —S(=O)$_2$NR$_2$ wherein each R is independently hydrogen or $C_{1-3}$ alkyl, and lower alkyl is as defined herein.

The term "trifluoromethyl sulfonyl" as used herein refers to a group of formula —S(=O)$_2$CF$_3$.

The term "trifluoromethyl sulfinyl" as used herein refers to a group of formula —S(=O)CF$_3$.

The term "trifluoromethyl sulfanyl" as used herein refers to a group of formula —SCF$_3$.

The term "nitro" as used herein refers to a group of formula —N$^+$(=O)O$^-$.

The term "carboxyl" as used herein refers to a group of formula —C(=O)R$_2$ wherein each R is independently hydrogen or $C_{1-3}$ alkyl, and lower alkyl is as defined herein.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "amino" as used herein denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "amido" as used herein denotes a group of the formula —C(=O)NR'R" or —NR'C(=O)R" wherein R' and R" are independently hydrogen, alkyl, alkoxy, cycloalkyl, heterocycloalkyl, aryl or heteroaryl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

Inhibitors of HCV Entry

The application provides a compound of formula I

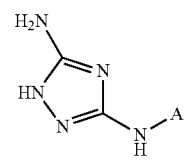

I wherein:
A is unsaturated or partially saturated monocyclic or bicyclic heteroaryl, optionally substituted with one or more A'; and each A' is independently halo, halo lower alkyl, lower alkyl, or oxo;
or a pharmaceutically acceptable salt thereof.

The application provides a compound of formula I, wherein A is pyridyl, optionally substituted with one or more A'.

The application provides the above compound of formula I, wherein A' is halo lower alkyl.

The application alternatively provides the above compound of formula I, wherein one A' is halo or two A' are halo.

The application provides a compound of formula I, wherein A is thiazolyl, optionally substituted with one or more A'.

The application provides the above compound of formula I, wherein A' is lower alkyl.

The application provides a compound of formula I, wherein A is thiophenyl, optionally substituted with one or more A'.

The application provides the above compound of formula I, wherein A' is halo.

The application provides a compound of formula I, wherein A is pyridazinone, optionally substituted with one or more A'.

The application provides the above compound of formula I, wherein one A' is lower alkyl and the other is halo.

The application provides a compound of formula I, wherein A is phthalazinone or imidazopyridinyl, optionally substituted with one or more A'.

The application provides a compound selected from the group consisting of:
$N^3$-(2-Chloro-pyridin-4-yl)-1H-[1,2,4]triazole-3,5-diamine;
$N^3$-(6-Trifluoromethyl-pyridin-3-yl)-1H-[1,2,4]triazole-3,5-diamine;
$N^3$-(2,6-Dichloro-pyridin-4-yl)-1H-[1,2,4]triazole-3,5-diamine;
$N^3$-(6-Trifluoromethyl-pyridin-2-yl)-1H-[1,2,4]triazole-3,5-diamine;
$N^3$-(4-tert-Butyl-thiazol-2-yl)-1H-[1,2,4]triazole-3,5-diamine;
$N^3$-(4-Trifluoromethyl-pyridin-2-yl)-1H-[1,2,4]triazole-3,5-diamine;
$N^3$-(5-Chloro-thiophen-3-yl)-1H-[1,2,4]triazole-3,5-diamine;
4-(5-Amino-1H-[1,2,4]triazol-3-ylamino)-6-chloro-2-methyl-2H-pyridazin-3-one;
6-(5-Amino-1H-[1,2,4]triazol-3-ylamino)-2H-phthalazin-1-one;
6-(5-Amino-1H-[1,2,4]triazol-3-ylamino)-2-methyl-2H-phthalazin-1-one;
$N^3$—Imidazo[1,2-a]pyridin-6-yl-1H-[1,2,4]triazole-3,5-diamine; and
$N^3$—Imidazo[1,2-a]pyridin-7-yl-1H-[1,2,4]triazole-3,5-diamine.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering a combination of antiviral agents that inhibits replication of HCV.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

The application provides a composition comprising a compound of Formula I and a pharmaceutically acceptable excipient.

The application provides the use of the compound of Formula I in the preparation of a medicament for the prevention of HCV.

The application provides the use of the compound of Formula I in the preparation of a medicament for the treatment of HCV.

The application provides any compound, composition, method or use as described herein.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v. 4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. TABLE I depicts examples of compounds according to generic Formula I:

TABLE I

| # | Nomenclature | Structure |
|---|---|---|
| 1 | $N^3$-(2-Chloro-pyridin-4-yl)-1H-[1,2,4]triazole-3,5-diamine | 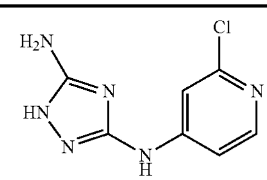 |
| 2 | $N^3$-(6-Trifluoromethyl-pyridin-3-yl)-1H-[1,2,4]triazole-3,5-diamine | 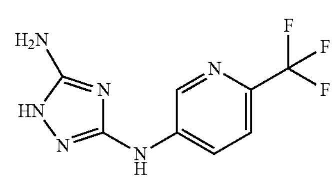 [SMILES: Nc1nc(Nc2ccc(C(F)(F)F)nc2)n[nH]1] |
| 3 | $N^3$-(2,6-Dichloro-pyridin-4-yl)-1H-[1,2,4]triazole-3,5-diamine | 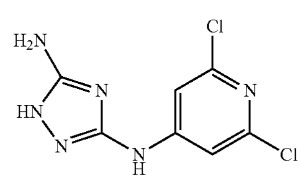 [SMILES: Nc1nc(Nc2cc(Cl)nc(Cl)c2)n[nH]1] |

TABLE I-continued

| # | Nomenclature | Structure |
|---|---|---|
| 4 | N³-(6-Trifluoromethyl-pyridin-2-yl)-1H-[1,2,4]triazole-3,5-diamine | 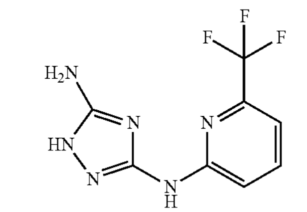 [SMILES: Nc1nc(Nc2cccc(C(F)(F)F)n2)n[nH]1] |
| 5 | N³-(4-tert-Butyl-thiazol-2-yl)-1H-[1,2,4]triazole-3,5-diamine | 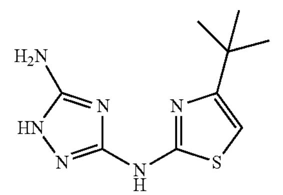 [SMILES: CC(C)(C)c1csc(Nc2n[nH]c(N)n2)n1] |
| 6 | N³-(4-Trifluoromethyl-pyridin-2-yl)-1H-[1,2,4]triazole-3,5-diamine | 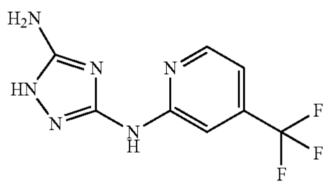 [SMILES: Nc1nc(Nc2cc(C(F)(F)F)ccn2)n[nH]1] |
| 7 | N³-(5-Chloro-thiophen-3-yl)-1H-[1,2,4]triazole-3,5-diamine | 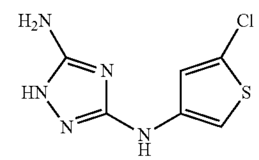 [SMILES: Nc1nc(Nc2csc(Cl)c2)n[nH]1] |
| 8 | 4-(5-Amino-1H-[1,2,4]triazol-3-ylamino)-6-chloro-2-methyl-2H-pyridazin-3-one | 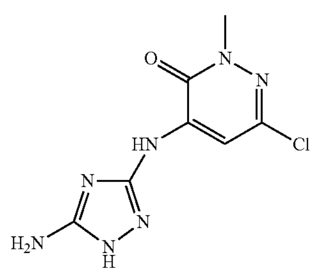 [SMILES: Cn1nc(Cl)cc(Nc2n[nH]c(N)n2)c1=O] |
| 9 | 6-(5-Amino-1H-[1,2,4]triazol-3-ylamino)-2H-phthalazin-1-one | 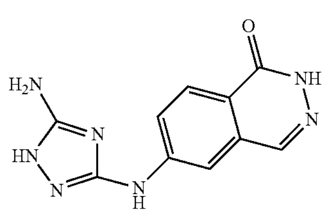 [SMILES: Nc1nc(Nc2ccc3c(=O)[nH]ncc3c2)n[nH]1] |
| 10 | 6-(5-Amino-1H-[1,2,4]triazol-3-ylamino)-2-methyl-2H-phthalazin-1-one | 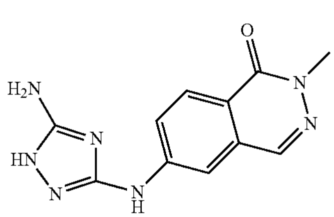 [SMILES: Cn1ncc2cc(Nc3n[nH]c(N)n3)ccc2c1=O] |
| 11 | N³-Imidazo[1,2-a]pyridin-6-yl-1H-[1,2,4]triazole-3,5-diamine | 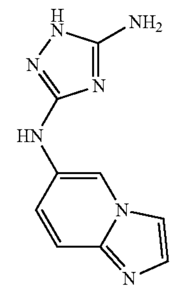 [SMILES: Nc1nc(Nc2ccc3nccn3c2)n[nH]1] |
| 12 | N³-Imidazo[1,2-a]pyridin-7-yl-1H-[1,2,4]triazole-3,5-diamine | 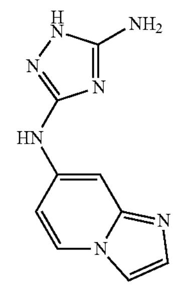 [SMILES: Nc1nc(Nc2ccn3ccnc3c2)n[nH]1] |

Synthesis

General Schemes

The following schemes depict general methods for obtaining compounds of Formula I.

Procedure 1

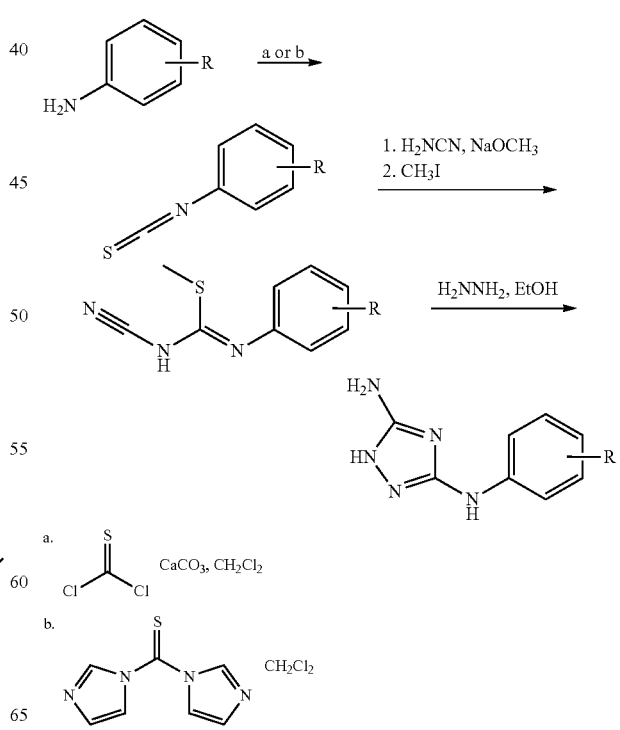

Procedure 2

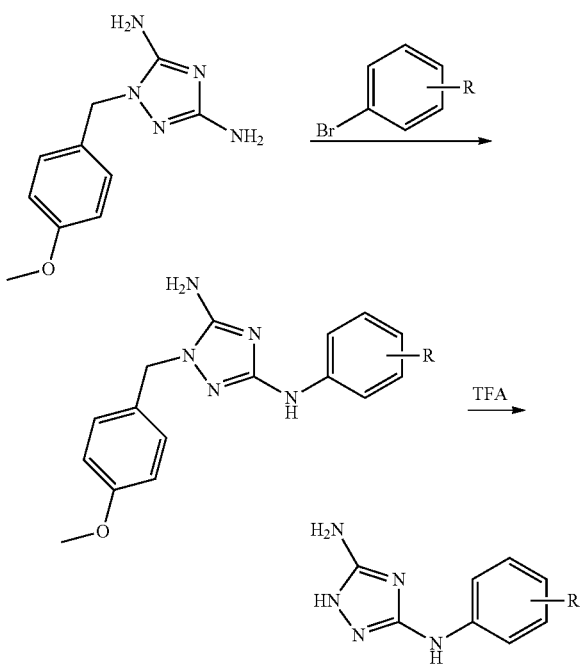

Procedure 3

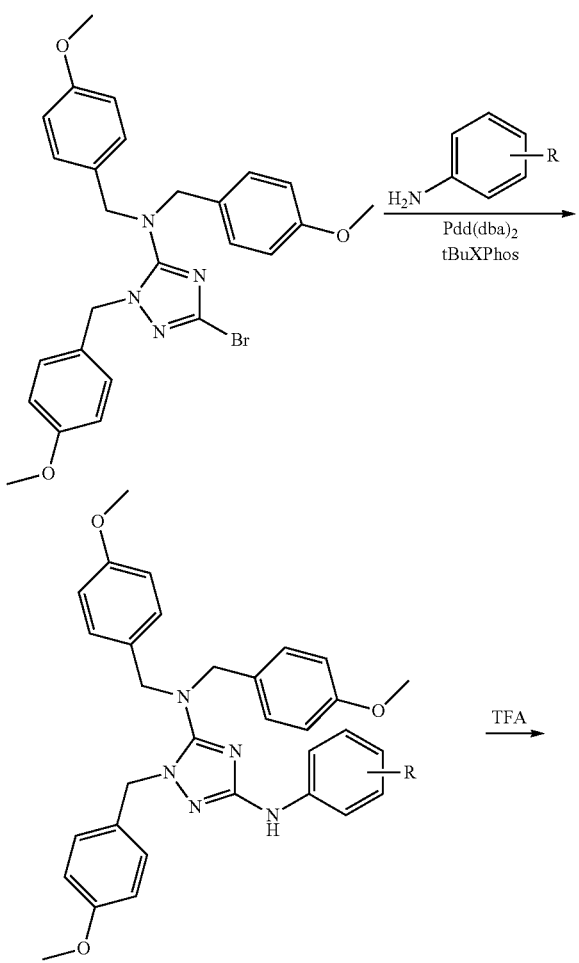

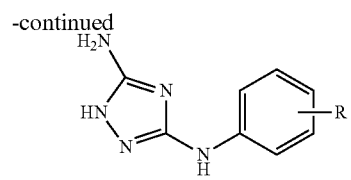

In the above General Schemes, each R can be independently halo, halo lower alkyl, lower alkyl, or oxo.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day.

Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment

Indications

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors, NS5A inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), micro-RNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/40381; WO00/56331, WO02/04425; WO03/007945; WO03/010141; WO03/000254; WO01/32153; WO00/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021927. Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropyl-magnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-$BuMe_2Si$ (TBDMS), tetra-n-butylammonium fluoride (TBAF), triethylamine (TEA or $Et_3N$), 2,2,6,6-tetramethyl-piperidine 1-oxyl (TEMPO), triflate or $CF_3SO_2$— (TO, trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, Nomenclature in Organic Chemistry, IUPAC 1979 Pergamon Press, Oxford.).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Preparative Examples

Example 1

N*3*-(2-Chloro-pyridin-4-yl)-1H-[1,2,4]triazole-3,5-diamine (Compound 1)

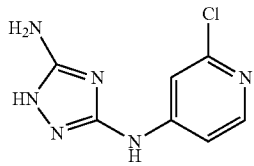 [SMILES: Nc1nc(Nc2ccnc(Cl)c2)n[nH]1]

2-chloro-4-isothiocyanatopyridine

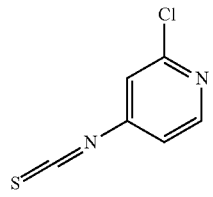 [SMILES: S=CC=Nc1ccnc(Cl)c1]

To a suspension of calcium carbonate (1.53 g, 15.3 mmol, Eq: 2.5) and thiophosgene (775 mg, 517 µl, 6.74 mmol, Eq: 1.1) in dichloromethane (10.0 ml)/water (10.0 ml) at 0°, was added 2-chloropyridin-4-amine (788 mg, 6.13 mmol, Eq: 1.00). The reaction was gradually warmed to room temperature and stirred overnight. Separated organic layer and dried over sodium sulfate. Chromatography (40 g Analogix, 0 to 10% ethyl acetate/hexane) gave 638 mg (61%) of desired product as a yellow solid.

(Z)-methyl N-2-chloropyridin-4-yl-N'-cyanocarbamimidothioate

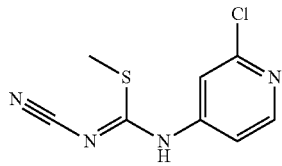

A solution of sodium methoxide (4.2 ml, 2.1 mmol, Eq: 1.19) was added to 2-chloro-4-isothiocyanatopyridine (81.3 mg, 1.93 mmol, Eq: 1.1) and stirred at room temperature for 15 minutes. 2-chloro-4-isothiocyanatopyridine (300 mg, 1.76 mmol, Eq: 1.00) was added to the reaction mixture and stirred for 1 hr. Iodomethane (568 mg, 250 µl, 4.00 mmol, Eq: 2.27) was added and the pale yellow solution was stirred overnight at room temperature. The resulting suspension was filtered to give 166 mg (42%) of desired product as an off-white solid.

N*3*-(2-Chloro-pyridin-4-yl)-1H-[1,2,4]triazole-3,5-diamine (Compound 1)

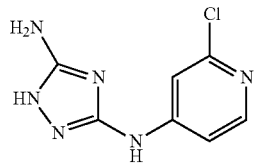

A solution of (Z)-methyl N-2-chloropyridin-4-yl-N'-cyanocarbamimidothioate (166 mg, 732 µmol, Eq: 1.00) and hydrazine (235 mg, 230 µL, 7.32 mmol, Eq: 10) in ethanol (5 mL) was heated at 65° C. for 2.5 hr, then at room temperature overnight. The resulting suspension was filtered to give 40 mg (28%) of desired product as a white solid. MS m/z 211 [M+H]

Example 2

N*3*-(6-Trifluoromethyl-pyridin-3-yl)-1H-[1,2,4]triazole-3,5-diamine (Compound 2)

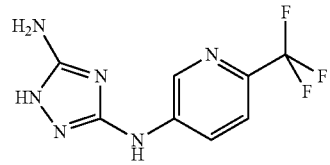 [SMILES: Nc1nc(Nc2ccc(C(F)(F)F)nc2)n[nH]1]

5-isothiocyanato-2-(trifluoromethyl)

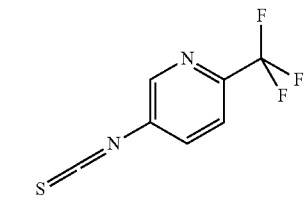 [SMILES: FC(F)(F)c1ccc(N=CC=S)cn1]

To a suspension of calcium carbonate (1.44 g, 14.4 mmol, Eq: 2.5) and thiophosgene (720 mg, 480 µl, 6.26 mmol, Eq: 1.08) in dichloromethane (10.0 ml)/water (10.0 ml) at 0°, was added 6-(trifluoromethyl)pyridin-3-amine (936 mg, 5.77 mmol, Eq: 1.00). The reaction was gradually warmed to room temperature. Separated organic layer and dried over sodium sulfate to give 1.0 g crude material. Chromatography (40 g Analogix, 0 to 10% ethyl acetate/hexane) gave 982 mg (83%) of desired product as a white solid.

(Z)-methyl N'-cyano-N-(6-(trifluoromethyl)pyridin-3-yl)carbamimidothioate

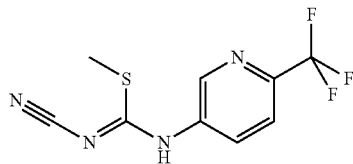 [SMILES: CS/C(=N\C#N)Nc1ccc(C(F)(F)F)nc1]

A solution of sodium methoxide (3.53 ml, 1.76 mmol, Eq: 1.2) was added to cyanamide (67.9 mg, 1.62 mmol, Eq: 1.1) and stirred at room temperature for 15 minutes. 5-isothiocyanato-2-(trifluoromethyl)pyridine (300 mg, 1.47 mmol, Eq: 1.00) was added to the reaction mixture and stirred for 1 hr. Iodomethane (459 mg, 202 µl, 3.23 mmol, Eq: 2.2) was added and the pale yellow solution was stirred overnight at room temperature. The solution was concentrated and chromatographed (50 to 75% EtOAc/Hex, 40 g Analogix) to give 227 mg (59%) of desired product as a white solid.

N*3*-(6-Trifluoromethyl-pyridin-3-yl)-1H-[1,2,4]triazole-3,5-diamine (Compound 2)

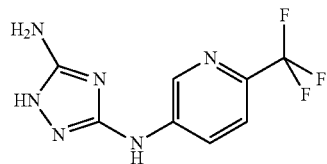

A solution of (Z)-methyl N'-cyano-N-(6-(trifluoromethyl)pyridin-3-yl)carbamimidothioate (227 mg, 872 µmol, Eq: 1.00) and hydrazine (281 mg, 275 µL, 8.76 mmol, Eq: 10.0) in ethanol (5 mL) was heated at 65° C. for 5 hr, then cooled to room temperature and stirred overnight. The resulting suspension was filtered and rinsed with cold methanol to give 44 mg (21%) of desired product as a white solid $^1$H NMR (300 MHz, DMSO) □: 11.43 (s, 1H), 9.51 (s, 1H), 8.72 (d, J=2 Hz, 1H), 8.17 (dd, J=9 Hz, 2 Hz, 1H), 7.70 (d, J=9 Hz, 1H), 6.04 (s, 2H) ppm

Example 3

N*3*-(2,6-Dichloro-pyridin-4-yl)-1H-[1,2,4]triazole-3,5-diamine (Compound 3)

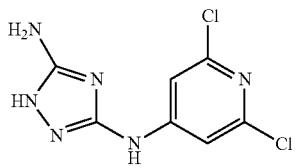

2,6-dichloro-4-isothiocyanatopyridine

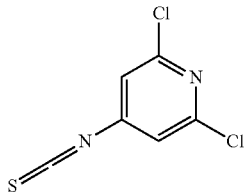 [SMILES: S=CC=Nc1cc(Cl)nc(Cl)c1]

A suspension of 2,6-dichloropyridin-4-amine (1 g, 6.13 mmol, Eq: 1.00), thiophosgene (2.82 g, 1.88 mL, 24.5 mmol, Eq: 4), triethylamine (145 mg, 200 µL, 1.43 mmol, Eq: 0.234) in benzene (20 mL) was heated at reflux for 4 hours. The orange slurry was filtered and washed with hexane. The filtrate was concentrated and chromatographed (40 g Redisep, 0 to 10% ethyl acetate/hexane) to give 827 mg (66%) of desired product as a colorless oil.

(Z)-methyl N'-cyano-N-(2,6-dichloropyridin-4-yl)carbamimidothioate

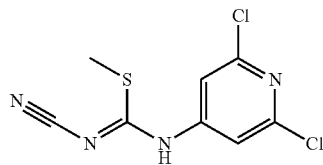

A solution of sodium methoxide (3.5 mL, 1.75 mmol, Eq: 1.2) was added to cyanamide (67.7 mg, 1.61 mmol, Eq: 1.1) and stirred at room temperature for 15 minutes. 2,6-dichloro-4-isothiocyanatopyridine (300 mg, 1.46 mmol, Eq: 1.00) in MeOH (3.5 mL) was added to the reaction mixture and stirred for 1 hr. Iodomethane (454 mg, 200 µL, 3.2 mmol, Eq: 2.19) was added and the reaction was stirred overnight at room temperature. The reaction was concentrated, suspended in dichloromethane, and the resulting suspension was filtered to give 371 mg (97%) of desired product as a white solid.

N*3*-(2,6-Dichloro-pyridin-4-yl)-1H-[1,2,4]triazole-3,5-diamine (Compound 3)

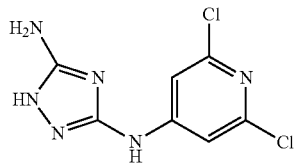

A solution of (Z)-methyl N'-cyano-N-(2,6-dichloropyridin-4-yl)carbamimidothioate (371 mg, 1.42 mmol, Eq: 1.00) and hydrazine (455 mg, 446 µL, 14.2 mmol, Eq: 10) in ethanol (10 mL) was heated at 65° C. overnight. The reaction was concentrated and the crude material chromatographed (23 g Supelco, 0 to 10% MeOH/CH2Cl2) to give 70 mg (10%) of desired product as a white solid.
MS m/z 245 [M+H]

Example 4

N*3*-(6-Trifluoromethyl-pyridin-2-yl)-1H-[1,2,4]triazole-3,5-diamine (Compound 4)

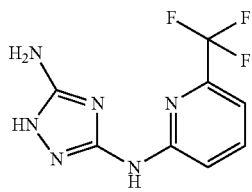 [SMILES: Nc1nc(Nc2cccc(C(F)(F)F)n2)n[nH]1]

isothiocyanato-6-(trifluoromethyl)pyridine

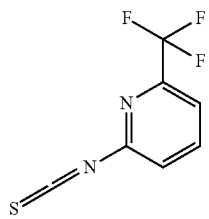 [SMILES: FC(F)(F)c1cccc(N=CC=S)n1]

To a suspension of calcium carbonate (1.56 g, 15.6 mmol, Eq: 2.57) and thiophosgene (780 mg, 520 µl, 6.78 mmol, Eq: 1.12) in dichloromethane (10 ml)/water (10 ml) at 0°, was added 6-(trifluoromethyl)pyridin-2-amine (985 mg, 6.08 mmol, Eq: 1.00). The reaction was gradually warmed to room temperature and stirred overnight. Separated organic layer and dried over sodium sulfate. Chromatography (40 g Analogix, 0 to 10% ethyl acetate/hexane) gave 965 mg (78%) of desired product as a colorless oil.

(Z)-methyl N'-cyano-N-(6-(trifluoromethyl)pyridin-2-yl)carbamimidothioate

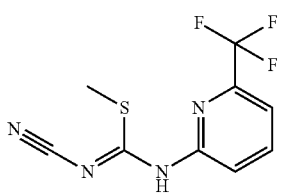 [SMILES: CS/C(=N\C#N)Nc1cccc(C(F)(F)F)n1]

A solution of sodium methoxide (3.5 ml, 1.75 mmol, Eq: 1.19) was added to cyanamide (67 mg, 1.59 mmol, Eq: 1.08) and stirred at room temperature for 15 minutes. 2-isothiocyanato-6-(trifluoromethyl)pyridine (300 mg, 1.47 mmol, Eq: 1.00) in methanol (3 mL) was added to the reaction mixture and stirred for 1 hr. Iodomethane (454 mg, 200 µl, 3.2 mmol, Eq: 2.18) was added and the pale yellow solution was stirred overnight at room temperature. The resulting suspension was filtered to give 72 mg white solid of desired product. The filtrate was concentrated and chromatographed (24 g Analogix, 0 to 50% Ethyl acetate/hex) to give 110 mg white solid of desired product. The products were combined to give 182 mg (48%) white solid.

N*3*-(6-Trifluoromethyl-pyridin-2-yl)-1H-[1,2,4]triazole-3,5-diamine (Compound 4)

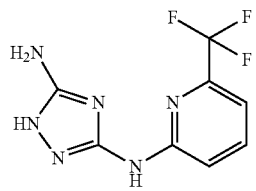

A solution of (Z)-methyl N'-cyano-N-(6-(trifluoromethyl)pyridin-2-yl)carbamimidothioate (182 mg, 699 µmol, Eq: 1.00) and hydrazine (224 mg, 220 µl, 6.99 mmol, Eq: 10) in ethanol (5 mL) was heated at 65° C. o/n. The resulting suspension was filtered to give 88 mg (52%) of desired product as a white solid.

$^1$H NMR (300 MHz, DMSO) □: 11.46 (1H, s), 9.73 (1H, s), 8.14 (d, J=9 Hz, 1H), 7.86 (t, J=8 Hz, 1H), 7.20 (d, J=7 Hz, 1H), 6.04 (s, 2H) ppm

Example 5

N*3*-(4-tert-Butyl-thiazol-2-yl)-1H-[1,2,4]triazole-3,5-diamine (Compound 5)

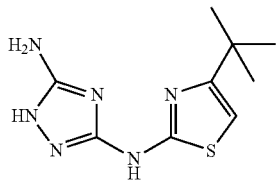

4-tert-butyl-2-isothiocyanatothiazole

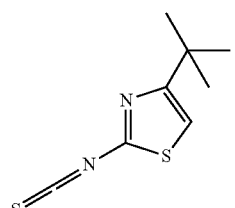

To a suspension of calcium carbonate (861 mg, 8.6 mmol, Eq: 2) and thiophosgene (555 mg, 370 µl, 4.83 mmol, Eq: 1.12) in dichloromethane (10.0 ml)/water (10.0 ml) at 0°, was added 4-tert-butylthiazol-2-amine (672 mg, 4.3 mmol, Eq: 1.00) The reaction was gradually warmed to room temperature and stirred overnight. Added 9 mL 1N HCl. Separated organic layer, dried over sodium sulfate, and chromatographed (40 g Analogix, 100% hex to 5% EtOAc/hex) to give 727 mg (85%) of desired product as a yellow oil.

27

(Z)-methyl N-4-tert-butylthiazol-2-yl-N'-cyanocarbamimidothioate

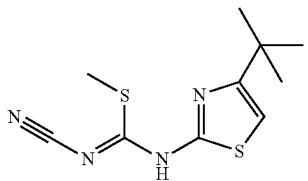 [SMILES: CS/C(=N\C#N)Nc1nc(C(C)(C)C)cs1]

Sodium methoxide (0.5M in methanol) (4.25 ml, 2.12 mmol, Eq: 1.2) was added to cyanamide (84 mg, 2.00 mmol, Eq: 1.13). After 15 minutes, a solution of 4-tert-butyl-2-isothiocyanatothiazole (350 mg, 1.76 mmol, Eq: 1.00) in methanol (5 mL) was added to the reaction. After 1 hr, methyl iodide (511 mg, 225 µl, 3.6 mmol, Eq: 2.04) was added and the reaction was stirred overnight at room temperature. The reaction mixture was concentrated and chromatographed (40 g Analogix, 20% EtOAc/hex to 50% EtOAc/hex) to give 142 mg (32%) of desired product as a white solid.

N*3*-(4-tert-Butyl-thiazol-2-yl)-1H-[1,2,4]triazole-3,5-diamine (Compound 5)

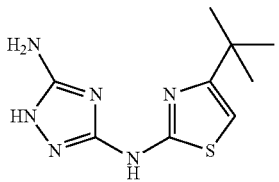 [SMILES: CC(C)(C)c1csc(Nc2n[nH]c(N)n2)n1]

A solution of (Z)-methyl N-4-tert-butylthiazol-2-yl-N'-cyanocarbamimidothioate (140 mg, 550 µmol, Eq: 1.00) and hydrazine (176 mg, 173 µl, 5.5 mmol, Eq: 10) in ethanol (5 mL) was heated at 70 deg o/. The reaction mixture was concentrated, chromatographed (11 g Supelco, 100% DCM to 10% MeOH/DCM) to give 61 mg (47%) of desired product as a white solid.

MS m/z 239 [M+H]

Example 6

N*3*-(4-Trifluoromethyl-pyridin-2-yl)-1H-[1,2,4]triazole-3,5-diamine (Compound 6)

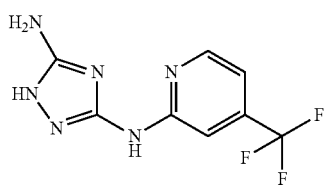 [SMILES: Nc1nc(Nc2cc(C(F)(F)F)ccn2)n[nH]1]

28

2-isothiocyanato-4-(trifluoromethyl)pyridine

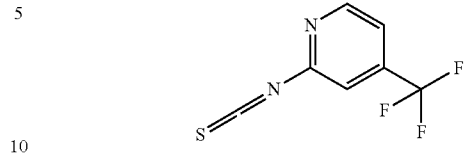

To a suspension of calcium carbonate (869 mg, 8.68 mmol, Eq: 2.5) and thiophosgene (450 mg, 300 µl, 3.91 mmol, Eq: 1.13) in dichloromethane (10.0 ml)/water (10.0 ml) at 0, was added 4-(trifluoromethyl)pyridin-2-amine (563 mg, 3.47 mmol, Eq: 1.00) The reaction was gradually warmed to room temperature and stirred overnight. Added 10 mL 1N HCl. Separated organic layer, dried over sodium sulfate, and chromatographed (60 g Analogix, 100% hex to 10% EtOAc.hex) to give 337 mg (48%) of desired product as an orange oil.

N-(methylthio(4-(trifluoromethyl)pyridin-2-ylamino)methyl)cyanamide

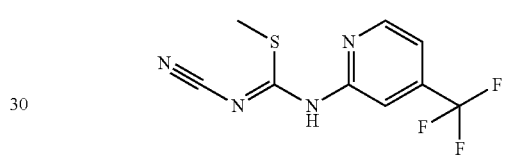

Sodium methoxide (0.5M in methanol) (4 ml, 2.00 mmol, Eq: 1.21) was added to cyanamide (78 mg, 1.86 mmol, Eq: 1.12). After 15 minutes, a solution of 2-isothiocyanato-4-(trifluoromethyl)pyridine (338 mg, 1.66 mmol, Eq: 1.00) in methanol (5 mL) was added. After 1 hr, methyl iodide (568 mg, 250 µl, 4.00 mmol, Eq: 2.42) was added and the reaction was stirred overnight at room temperature. The reaction mixture was concentrated and chromatographed (40 g Analogix, 10% to 50% EtOAc/hex) to give 155 mg (36%) of desired product as an orange solid.

N*3*-(4-Trifluoromethyl-pyridin-2-yl)-1H-[1,2,4]triazole-3,5-diamine (Compound 6)

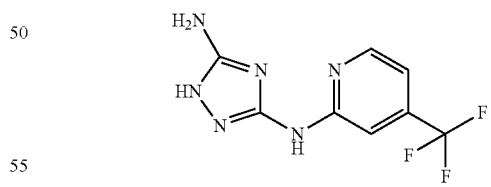

To a solution of N-(methylthio(4-(trifluoromethyl)pyridin-2-ylamino)methyl)cyanamide (155 mg, 0.591 mmol, Eq: 1) in methanol (5 mL) was added hydrazine (189 mg, 186 µl, 5.91 mmol, Eq: 10). The reaction mixture was heated at 60 deg o/n. The reaction mixture was concentrated and chromatographed (11 g Supelco, 10% MeOH/DCM) to give 34 mg yellow solid, containing product and impurities. Further purification (SFC) gave 15 mg (10%) of desired product as a pale yellow solid.

MS m/z 245 [M+H]

Example 7

N3-(5-chlorothiophen-3-yl)-1H-1,2,4-triazole-3,5-diamine (Compound 7)

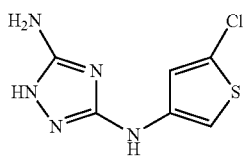 [SMILES: Nc1nc(Nc2csc(Cl)c2)n[nH]1]

5-Chlorothiophene-3-carboxylic acid

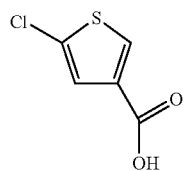

In a 1 L round-bottomed flask, N-chlorosuccinimide (23.5 g, 176 mmol, Eq: 1.00) and thiophene-3-carboxylic acid (17.5 g, 137 mmol, Eq: 0.776) were combined with acetic acid (200 mL) to give a white suspension. The reaction mixture was refluxed for 4 hours. After this time, the reaction mixture was cooled to room temperature. The reaction mixture was combined with ice water. The resulting mixture was extracted several times with methylene chloride. The combined organic extracts were then treated with an equal volume of 1.0 N aqueous sodium hydroxide solution. This aqueous mixture was washed once with methylene chloride. The aqueous phase was acidified with concentrated HCl to precipitate a white solid. This precipitate was filtered, and then thoroughly dried under vacuum with heating at 65° C. to afford 5-chlorothiophene-3-carboxylic acid (14 g, 49%) as a cream colored powder.

tert-Butyl 5-chlorothiophen-3-ylcarbamate

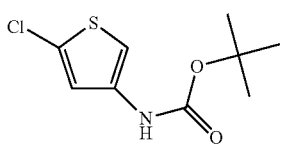

In a 500 mL round-bottomed flask, 5-chlorothiophene-3-carboxylic acid (5.0 g, 30.8 mmol, Eq: 1.00), and triethylamine (4.71 mL, 33.8 mmol, Eq: 1.1) were combined with DMF (50 mL) to give a light brown solution. The reaction mixture was cooled to 0° C. in an ice-water bath, and diphenylphosphoryl azide (9.31 g, 7.29 ml, 33.8 mmol, Eq: 1.1) was added dropwise via a syringe. The reaction mixture was stirred at 0° C. for 15 minutes, and then warmed to 40° C. The reaction mixture was stirred at 40° C. for 4 hours. After this time, TLC indicated complete consumption of the starting material to a non-polar intermediate. To the reaction mixture was added tert-butanol (14.7 mL, 154 mmol, Eq: 5), and the mixture was heated at 90° C. overnight. In the morning, the reaction mixture was returned to 65° C. then concentrated on the rotary evaporator at this temperature. The crude product was purified by flash chromatography (300 g Analogix column, 10%-35% ethyl acetate-hexanes) to afford tert-butyl 5-chlorothiophen-3-ylcarbamate. The final product contained a significant non-polar impurity as indicated by $^1$H NMR analysis.

5-Chlorothiophen-3-amine

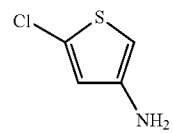

In a 250 mL round-bottomed flask, tert-butyl 5-chlorothiophen-3-ylcarbamate (1.0 g, 4.28 mmol, Eq: 1.00) and a 4.0 M solution of HCl in dioxne (9 mL, 4.5 mmol, Eq: 1.05) were combined with dioxane (5 mL) to give a colorless solution. After only 15 minutes, the reaction mixture became cloudy with a precipitate. The reaction mixture was stirred at room temperature over 4 hours. After this time, the reaction mixture was a thick, cream colored slurry. The reaction mixture was filtered, and the collected solids were thoroughly dried under vacuum. The crude product was then combined with methylene chloride and saturated aqueous sodium bicarbonate. The organic phase was dried, filtered and concentrated to give 5-chlorothiophen-3-amine as a tan oil (270 mg, 47%).

2-Chloro-4-isothiocyanatothiophene

In a 250 mL round-bottomed flask, 5-chlorothiophen-3-amine (0.5 g, 3.74 mmol, Eq: 1.00) and 1,1'-thiocarbonyldiimidazole (1.33 g, 7.49 mmol, Eq: 2.0) were combined with methylene chloride (23.4 mL) to give a light brown suspension. This suspension was stirred at room temperature for 10 minutes. During this time, the starting materials did not dissolve. Imidazole (225 mg, 3.74 mmol) was added to the reaction mixture, and the reaction mixture quickly became a homogeneous light brown solution within 30 seconds. The reaction mixture was stirred over night at room temperature. In the morning, the reaction mixture was filtered, and then concentrated over silica gel. The silica gel supported crude product was loaded onto a 120 gram SiliCycle column. Flash chromatography (100% hexanes) was used to isolate 2-chloro-4-isothiocyanatothiophene (430 mg, 65%).

(Z)-Methyl N-5-chlorothiophen-3-yl-N'-cyanocarbamimidothioate

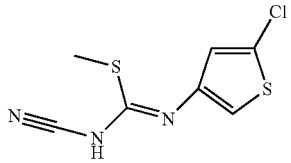

A 50 mL round-bottom flask was charged with cyanamide (52.7 mg, 1.25 mmol, Eq: 1.1) and a 0.5 M solution of sodium methoxide in MeOH (2.5 mL, 1.25 mmol, Eq: 1.2). The resulting mixture was stirred for 15 minutes at room temperature. Separately, 2-chloro-4-isothiocyanatothiophene (200 mg, 1.14 mmol, Eq: 1.00) was combined with methanol (4.55 mL) with stirring. The cyanamide mixture was transferred to the starting material mixture via a syringe. The reaction mixture was stirred for one hour at room temperature, then iodomethane (0.162 g, 0.070 mL, 1.14 mmol, Eq: 1.0) was added at room temperature. The reaction mixture was stirred for two hours at room temperature. After this time a significant amount of white solid precipitated. The product was filtered off then washed with 2 mL of methanol to afford (Z)-methyl N-5-chlorothiophen-3-yl-N'-cyanocarbamimidothioate (52 mg, 20%).

N3-(5-chlorothiophen-3-yl)-1H-1,2,4-triazole-3,5-diamine (Compound 7)

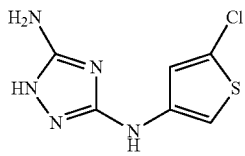 [SMILES: Nc1nc(Nc2csc(Cl)c2)n[nH]1]

In a 50 mL round-bottomed flask, (Z)-methyl N-5-chlorothiophen-3-yl-N'-cyanocarbamimidothioate (52 mg, 224 µmol, Eq: 1.00) was combined with ethanol (2.99 mL) to give a colorless solution. Hydrazine (80 µL, 2.55 mmol, Eq: 11.4) was added. The reaction mixture was refluxed for two hours, and then cooled to room temperature. The reaction mixture was stirred for an additional 14 hours at room temperature. The solvent was evaporated, and the crude product was combined with 10% methanol in chloroform. The solution was filtered, and the filtrate was concentrated to afford N3-(5-chlorothiophen-3-yl)-1H-1,2,4-triazole-3,5-diamine (51 mg, 98%) as a light yellow solid. MS cald. for $C_6H_6ClN_5S$ [(M+H)$^+$]: 216, obsd. 216.0.

Example 8

4-(5-Amino-1H-[1,2,4]triazol-3-ylamino)-6-chloro-2-methyl-2H-pyridazin-3-one (Compound 8)

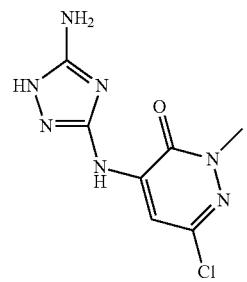 [SMILES: Cn1nc(Cl)cc(Nc2n[nH]c(N)n2)c1=O]

1-(4-Methoxy-benzyl)-1H-[1,2,4]triazole-3,5-diamine

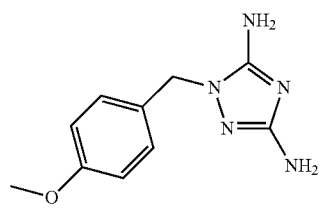 [SMILES: COc1ccc(Cn2nc(N)nc2N)cc1]

In a 500 mL round-bottomed flask, 1H-1,2,4-triazole-3,5-diamine (1.5 g, 15.1 mmol, Eq: 1.00) and sodium methoxide 1M (33.3 ml, 16.7 mmol, Eq: 1.1) were combined with MeOH (100 ml) to give a colorless turbid solution. The reaction mixture was stirred for 4 hr and stripped to a gray solid. Suspended in 30 ml DMF and 1-(chloromethyl)-4-methoxybenzene (2.42 g, 2.1 ml, 15.4 mmol, Eq: 1.02) was added. The dark brown suspension was stirred at 25 C for 60 hrs under argon. The reaction was diluted with water (35 ml) and extracted with EtOAc (3×50 ml). The organic layers were combined, washed with H$_2$O (1×25 mL), sat NaCl (1×50 ml), dried over Na2SO4 and concentrated in vacuo to a white pasty solid. Dried under vacuum while gently heating to remove residual DMF and PMB-Cl. The crude material was purified by flash chromatography (silica gel, 80 g, 0% to 10% MeOH in DCM) to give 457 mg of desired product as a yellow solid (14%). MS (m+1)=220.

4-[5-Amino-1-(4-methoxybenzyl)-1H-[1,2,4]triazol-3-ylamino]-6-chloro-2-methyl-2H-pyridazin-3-one

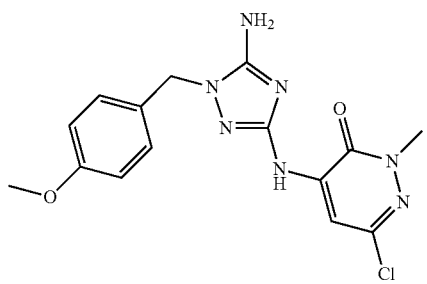

To a 10 mL microwave vial was added 1-(4-methoxybenzyl)-1H-1,2,4-triazole-3,5-diamine (49 mg, 223 µmol, Eq: 1.00), 4-bromo-6-chloro-2-methylpyridazin-3(2H)-one (59.9 mg, 268 µmol, Eq: 1.2) and K₂CO₃ (92.7 mg, 670 µmol, Eq: 3) in NMP (1 ml). The vial was capped and heated in the microwave at 130° C. for 30 min. The reaction mixture was diluted with 25 mL H₂O and extracted with dichloromethane (3×50 mL). The organic layers were combined, washed with H₂O (1×25 mL), brine (1×20 mL), dried over Na₂SO₄ and concentrated in vacuo. The crude material was purified by flash chromatography (silica gel, 12 g, 0% to 10% methanol in dichloromethane) to afford 72 mg (89%) of the desired product as a white solid.

MS +m/z: 362.0/364.0. (M+1)

4-(5-Amino-1H-[1,2,4]triazol-3-ylamino)-6-chloro-2-methyl-2H-pyridazin-3-one (Compound 8)

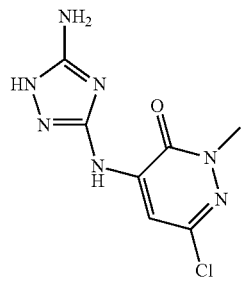

In a 250 mL round-bottomed flask, 4-(5-amino-1-(4-methoxybenzyl)-1H-1,2,4-triazol-3-ylamino)-6-chloro-2-methylpyridazin-3(2H)-one (73 mg, 202 µmol, Eq: 1.00) was combined with TFA (3 ml) to give a dark red solution. The reaction mixture was heated to 65° C. and stirred for 17 h. The crude reaction mixture was concentrated and the residue was diluted with sat NaHCO₃ and filtered. The solid was triturated with dichloromethane (3×10 mL). The solid was washed with water and dried under vacuum. The residue was suspended in methanol and filtered to remove an insoluble brown solid. The filtrate was stripped in vacuo to afford 43 mg (90%) of the desired product as an orange solid. MS +m/z: 241.9/244.1. (M+1)

Example 9

6-(5-Amino-1H-[1,2,4]triazol-3-ylamino)-2H-phthalazin-1-one (Compound 9)

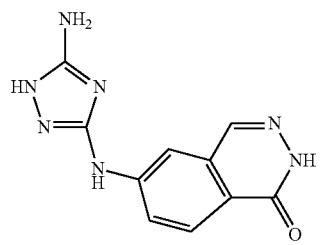 [SMILES: Nc1nc(Nc2ccc3c(=O)[nH]ncc3c2)n[nH]1]

6-Amino-2H-pyridazin-1-one

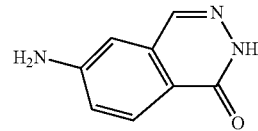

In a 10 ml seal tube, 6-bromo-2H-pyridazin-1-one (108 mg, 480 µmol, Eq: 1.00), NH₄OH (931 mg, 1.03 ml, 7.97 mmol, Eq: 16.6) and copper powder (30.5 mg, 480 µmol, Eq: 1.00) were combined with isopropyl alcohol (1 ml) to give a light brown suspension. The tube was sealed and the reaction was heated to 100° C. overnight. The crude reaction mixture was concentrated in vacuo. The reaction mixture was diluted with sat NH₄Cl and dichloromethane. The 2 phase mixture was filtered, the filtrate was separated and the aqueous extracted with dichloromethane (3×30 ml). SiO₂ was added to the aqueous phase and concentrated. The solid was suspended in hot dichloromethane/methanol 9:1 and sonicated. Filtered and washed the filter cake with warm dichloromethane/methanol 9:1. The filtrate was combined with the dichloromethane extracts and stripped to a light yellow powder. The powder was dried under vacuum at 25° C. for 1 hour to afford 62 mg (80%) of the desired product. MS +m/z: 162.1. (M+1)

6-Isothiocyanato-2H-pyridazin-1-one

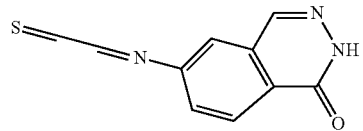 [SMILES: O=c1[nH]ncc2cc(N=CC=S)ccc12]

In a 100 mL pear-shaped flask, 6-aminophthalazin-1(2H)-one (60 mg, 372 µmol, Eq: 1.00) and calcium carbonate (130 mg, 1.3 mmol, Eq: 3.5) were combined with dichloromethane (5 ml) and water (5.00 ml) to give a light brown suspension. Thiophosgene (47.1 mg, 31.4 µl, 410 µmol, Eq: 1.1) was added and the reaction mixture was stirred at 25° C. for 5 days. The reaction mixture was diluted with dichloromethane, separated and the aqueous was extracted with dichloromethane. The organic layer was dried over Na₂SO₄ and concentrated in vacuo to give a yellow solid. The product was dried under vacuum at 25 C for 2 hours and used in the subsequent reaction without any further purification.

MS +m/z: 204.0. (M+1)

6-((Methyl-$\lambda^4$sulfanylidene)-methyl-cyanamide)-2H-pyridazin-1-one

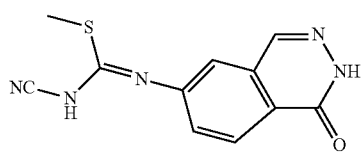 [SMILES: CSC(=Nc1ccc2c(=O)[nH]ncc2c1)NC#N]

In a 250 mL round-bottomed flask, 6-isothiocyanatophthalazin-1(2H)-one (75 mg, 369 μmol, Eq: 1.00) and sodium hydrogencyanamide (26.0 mg, 406 μmol, Eq: 1.1) were combined with methanol (2 ml) and dichloromethane (1 ml) to give an orange suspension. The reaction mixture was stirred at 25° C. for 3 h, then methyl iodide (62.9 mg, 27.71 μl, 443 μmol, Eq: 1.2) was added. The reaction mixture was stirred at 25° C. for 16 h. The crude reaction mixture was concentrated in vacuo and the orange solid was used in the subsequent reaction without further purification.

MS +m/z: 260.0. (M+1)

6-(5-Amino-1H-[1,2,4]triazol-3-ylamino)-2H-phthalazin-1-one (Compound 9)

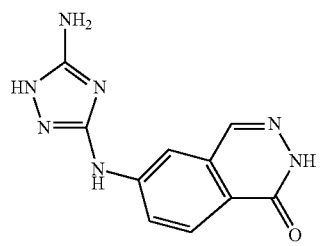 [SMILES: Nc1nc(Nc2ccc3c(=O)[nH]ncc3c2)n[nH]1]

In a 250 mL round-bottomed flask, 6-((Methyl-□⁴sulfanylidene)-methyl-cyanamide)-2H-pyridazin-1-one (95 mg, 366 μmol, Eq: 1.00) was combined with ethanol (3 ml) to give a light yellow suspension. Hydrazine monohydrate (183 mg, 178 μL 3.66 mmol, Eq: 10) was added and the reaction mixture was heated to 70° C. and stirred for 3 h. The crude reaction mixture was concentrated in vacuo and the residue was dried overnight under vacuum. The light brown solid was triturated with dichloromethane/methanol/NH₄OH (60:10:1), washed with methanol and dried under vacuum. The solid was triturated with methanol and 1M HCl while heating. The warm suspension was filtered and the brown solid was dried under vacuum to afford 6 mg (7%) of the desired product.

MS −m/z: 242.0. (M−1)

Example 10

6-(5-Amino-1H-[1,2,4]triazol-3-ylamino)-2-methyl-2H-phthalazin-1-one (Compound 10)

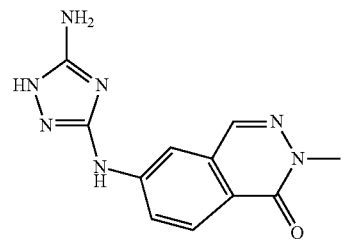 [SMILES: Cn1ncc2cc(Nc3n[nH]c(N)n3)ccc2c1=O]

6-Bromo-2-methyl-2H-pyridazin-1-one

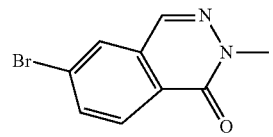

In a 50 mL pear-shaped flask, 6-bromophthalazin-1(2H)-one (214 mg, 951 μmol, Eq: 1.00) and Cs₂CO₃ (372 mg, 1.14 mmol, Eq: 1.20) were combined with DMF (3 ml) to give a light brown suspension. Methyl iodide (202 mg, 89.0 μl, 1.43 mmol, Eq: 1.50) was added and the reaction mixture was stirred at 25° C. for 20 h. The reaction was diluted with dichloromethane and water. The aqueous layer was back-extracted with dichloromethane (3×20 mL). The combined organic layers were washed with H₂O (1×25 mL), dried over Na₂SO₄ and concentrated in vacuo. The crude material was recrystallized from dichloromethane to give a light yellow solid. The solid was dried under vacuum to afford 112 mg (49%) of the desired product as a light yellow crystalline solid.

MS +m/z: 239/241 (M+1)

6-Amino-2-methyl-2H-pyridazin-1-one

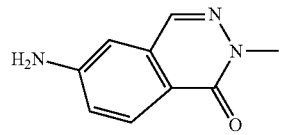

In a 10 mL sealed tube, 6-bromo-2-methylphthalazin-1(2H)-one (112 mg, 468 μmol, Eq: 1.00) and copper powder (29.8 mg, 468 μmol, Eq: 1.00) were combined with 2-Propanol (1 ml) to give a light brown suspension. Ammonium hydroxide (908 mg, 1.01 ml, 7.78 mmol, Eq: 16.6) was added and the reaction mixture was heated to 100° C. and stirred for 21 h in a sealed tube. Cooled and diluted with dichloromethane. Na₂SO₄ was added and the mixture was filtered. The colorless filtrate was concentrated to a tan solid and dried under vacuum at 25° C. overnight to afford 63 mg (77%) of the desired product as an off white solid. The material was used in the subsequent reaction without any further purification.

MS +m/z: 176 (M+1)

6-Isothiocyanato-2-methyl-2H-pyridazin-1-one

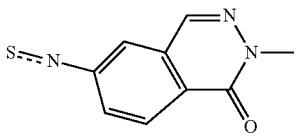

In a 100 mL pear-shaped flask, 6-amino-2-methylphthalazin-1(2H)-one (63 mg, 360 μmol, Eq: 1.00) and calcium carbonate (126 mg, 1.26 mmol, Eq: 3.5) were combined with dichloromethane (3 ml) and water (3 ml) to give a light brown suspension. Thiophosgene (45.5 mg, 30.3

µl, 396 µmol, Eq: 1.1) was added and the reaction mixture was stirred at 25° C. for 23 h. LC-MS at t=23 h showed the reaction was complete. The reaction mixture was diluted with dichloromethane, separated and the aqueous was extracted with dichloromethane. The organic layer was dried over Na$_2$SO$_4$ and concentrated in vacuo to give a fluffy white solid. The product was dried under vacuum and used in the subsequent reaction without any further purification.

MS +m/z: 218.0. (M+1)

6-((Methyl-λ$^4$sulfanylidene)-methyl-cyanamide)-2-methyl-2H-pyridazin-1-one

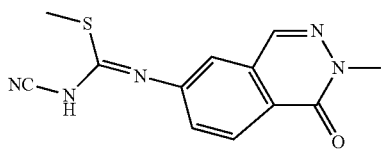 [SMILES: CSC(=Nc1ccc2c(=O)n(C)ncc2c1)NC#N]

In a 250 mL round-bottomed flask, 6-isothiocyanato-2-methylphthalazin-1(2H)-one (78 mg, 359 µmol, Eq: 1.00) and sodium hydrogencyanamide (25.3 mg, 395 µmol, Eq: 1.1) were combined with methanol (4 ml) and dichloromethane (1.5 ml) to give a yellow suspension. The reaction mixture was stirred at 25° C. for 2 h, then methyl iodide (61.2 mg, 26.9 µl, 431 µmol, Eq: 1.2) was added. The reaction mixture was stirred at 25° C. for 19 h, concentrated in vacuo to a light yellow solid and used in the subsequent reaction without further purification.

MS +m/z: 274.0. (M+1)

6-(5-Amino-1H-[1,2,4]triazol-3-ylamino)-2-methyl-2H-phthalazin-1-one (Compound 10)

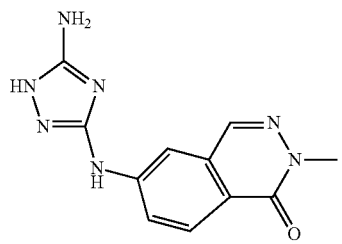 [SMILES: Cn1ncc2cc(Nc3n[nH]c(N)n3)ccc2c1=O]

In a 100 mL pear-shaped flask, 6-((Methyl-□$^4$sulfanylidene)-methyl-cyanamide)-2-methyl-2H-pyridazin-1-one (98 mg, 359 µmol, Eq: 1.00) and hydrazine monohydrate (179 mg, 174 µL 3.59 mmol, Eq: 10) were combined with ethanol (3 ml) to give a light yellow suspension and the reaction mixture was heated to 70° C. for 3 hours. The crude reaction mixture was concentrated in vacuo and acidified with 1M HCl. The solid was filtered and washed with water. The solid was suspended in methanol and concentrated NH$_4$OH was added. The yellow suspension was concentrated, filtered and washed with water. The tan solid was dried overnight at 45° C. under vacuum to afford 44 mg (48%) of the desired product as an off white solid.

MS +m/z: 258.0. (M+1)

Example 11

N*3*-Imidazo[1,2-a]pyridin-6-yl-1H-[1,2,4]triazole-3,5-diamine (Compound 11)

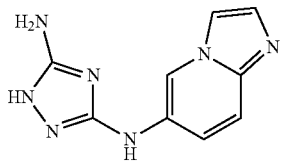 [SMILES: Nc1nc(Nc2ccc3nccn3c2)n[nH]1]

3,5-Dibromo-1-(4-methoxy-benzyl)-1H-[1,2,4]triazole

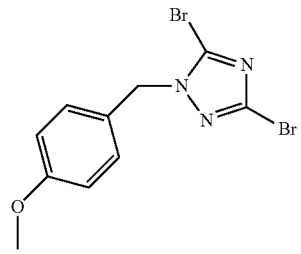 [SMILES: COc1ccc(Cn2nc(Br)nc2Br)cc1]

In a 100 mL round-bottomed flask, 3,5-dibromo-1H-1,2,4-triazole (5 g, 22.0 mmol, Eq: 1.00), 1-(chloromethyl)-4-methoxybenzene (3.45 g, 22.0 mmol, Eq: 1) and N-ethyl-N-isopropylpropan-2-amine (5.7 g, 44.1 mmol, Eq: 2) were combined with acetonitrile (101 ml) to give a light yellow solution. Potassium iodide (1.83 g, 11.0 mmol, Eq: 0.5) was added. The mixture was heated to reflux for 2 hours. The reaction mixture was cooled and diluted with EtOAc (100 mL), washed with H$_2$O (50 mL) and brine (50 mL). The organic layer was dried over anhydrous MgSO$_4$, filtered and volatiles were removed under reduced pressure to yield an oil from which the compound was isolated by column chromatography (Hexanes/EtOAc=70/30) to give 7.3 g of desired product (95%).

5-Bromo-2-(4-methoxy-benzyl)-2H-[1,2,4]triazol-3-yl]-bis-(4-methoxy-benzyl)-amine

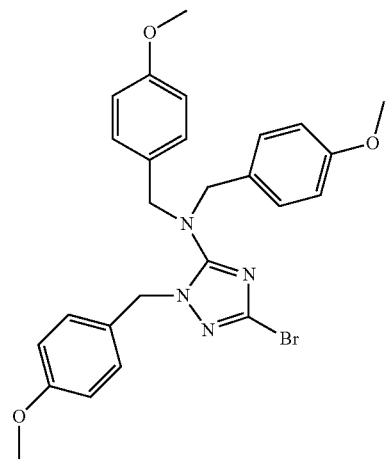 [SMILES: COc1ccc(CN(Cc2ccc(OC)cc2)c2nc(Br)nn2Cc2ccc(OC)cc2)cc1]

In a 10 mL sealed tube, 3,5-dibromo-1-(4-methoxybenzyl)-1H-1,2,4-triazole (400 mg, 1.15 mmol, Eq: 1.00) and bis(4-methoxybenzyl)amine (356 mg, 1.38 mmol, Eq: 1.20) were combined, the mixture was heated to 140° C. for overnight. The reaction mixture was cooled to room temperature, added CH$_2$Cl$_2$ (50 mL) washed with H$_2$O (50 mL) and brine (50 mL). The organic layer was dried over anhydrous MgSO$_4$, filtered and volatiles were removed under reduced pressure. The compound was isolated by column chromatography to give a light yellow solid 300 mg (50%). MH+ 525.1

N*3*-Imidazo[1,2-a]pyridin-6-yl-1,N*5*,N*5*-tris-(4-methoxy-benzyl)-1H-[1,2,4]triazole-3,5-diamine

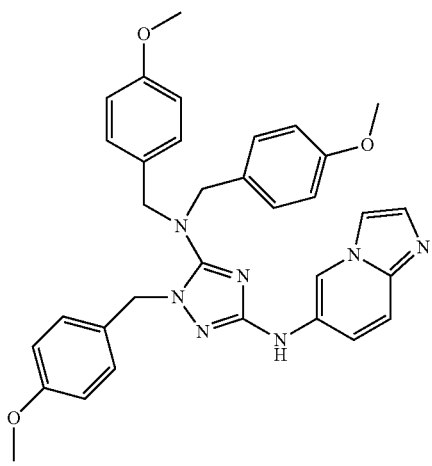 [SMILES: COc1ccc(CN(Cc2ccc(OC)cc2)c2nc(Nc3ccc4nccn4c3)nn2Cc2ccc(OC)cc2)cc1]

In 25 mL sealed tube, sodium 2-methylpropan-2-olate (60.2 mg, 626 μmol, Eq: 1.20), bis(dibenzylideneacetone) palladium (30.0 mg, 52.2 μmol, Eq: 0.1) and 2-di-tert-butyl (2',4',6'-triisopropylbiphenyl-2-yl)phosphine (22.2 mg, 52.2 μmol, Eq: 0.1) were combined with toluene (5.00 mL) to give a dark brown suspension. 3-Bromo-N,N,1-tris(4-methoxybenzyl)-1H-1,2,4-triazol-5-amine (278 mg, 522 μmol, Eq: 1.00) and imidazo[1,2-a]pyridin-6-amine (69.5 mg, 522 μmol, Eq: 1.00) were added. The reaction mixture was degassed with argon for 15 min, and then heated to 110° C. for 3 hours. The reaction mixture was cooled and diluted with EtOAc (50 mL), washed with H$_2$O (25 mL) and brine (25 mL). The organic layer was dried over anhydrous MgSO$_4$, filtered and volatiles were removed under reduced pressure to yield the crude product 280 mg (93%). MH+ 576.4

N*3*-Imidazo[1,2-a]pyridin-6-yl-1H-[1,2,4]triazole-3,5-diamine (Compound 11)

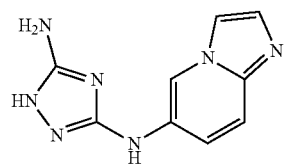 [SMILES: Nc1nc(Nc2ccc3nccn3c2)n[nH]1]

In a 10 mL round bottle, N*3*-imidazo[1,2-a]pyridin-6-yl-1,N*5*,N*5*-tris-(4-methoxy-benzyl)-1H-[1,2,4]triazole-3,5-diamine (280 mg, 486 μmol, Eq: 1.00) was combined with TFA (5.00 mL) to give a colorless solution. The resulting solution was heated to reflux overnight, the reaction mixture was concentrated, and then diluted with EtOAc (30 mL). The solution was washed with saturated NaHCO$_3$, organic layer was dried over anhydrous MgSO$_4$, filtered and volatiles were removed under reduced pressure. The compound was isolated by preparative TLC to give an off-white solid 56 mg (54%). MH+ 215.9

Example 12

N*3*-Imidazo[1,2-a]pyridin-7-yl-1H-[1,2,4]triazole-3,5-diamine (Compound 12)

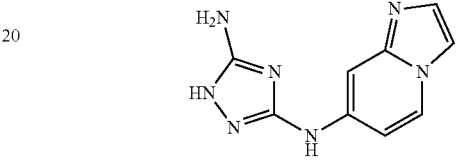

N*3*-Imidazo[1,2-a]pyridin-7-yl-1,N*5*,N*5*-tris-(4-methoxy-benzyl)-1H-[1,2,4]triazole-3,5-diamine

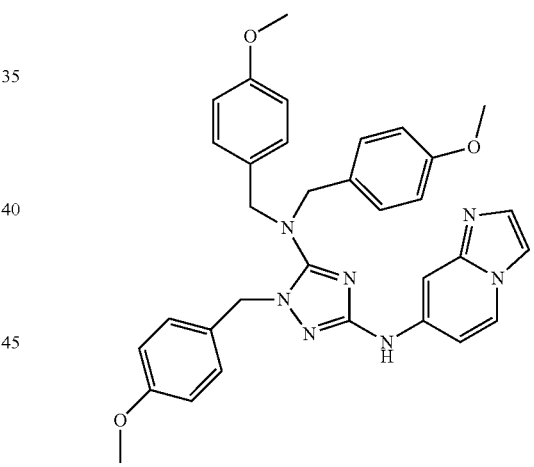

In a 25 mL sealed tube, sodium 2-methylpropan-2-olate (60.2 mg, 626 μmol, Eq: 1.20), bis(dibenzylideneacetone) palladium (30.0 mg, 52.2 μmol, Eq: 0.1) and 2-di-tert-butyl (2',4',6'-triisopropylbiphenyl-2-yl)phosphine (22.2 mg, 52.2 μmol, Eq: 0.1) were combined with toluene (5.00 mL) to give a dark brown suspension. 3-Bromo-N,N,1-tris(4-methoxybenzyl)-1H-1,2,4-triazol-5-amine (278 mg, 522 μmol, Eq: 1.00) and imidazo[1,2-a]pyridin-7-amine (69.5 mg, 522 μmol, Eq: 1.00) were added. The reaction mixture was degassed with argon for 15 min, and then heated to 110° C. for 3 hours. The reaction mixture was cooled and diluted with EtOAc (50 mL), washed with H$_2$O (25 mL) and brine (25 mL). The organic layer was dried over anhydrous MgSO$_4$, filtered and volatiles were removed under reduced pressure to yield the crude product 290 mg (97%). MH+ 576.4

N*3*-Imidazo[1,2-a]pyridin-7-yl-1H-[1,2,4]triazole-3,5-diamine (Compound 12)

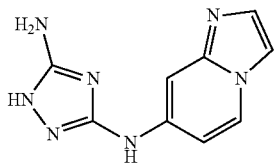 [SMILES: Nc1nc(Nc2ccn3ccnc3c2)n[nH]1]

In a 10 mL round bottle, N*3*-imidazo[1,2-a]pyridin-7-yl-1,N*5*,N*5*-tris-(4-methoxy-benzyl)-1H-[1,2,4]triazole-3,5-diamine (300 mg, 521 µmol, Eq: 1.00) was combined with TFA (5.00 mL) to give a colorless solution. The resulting solution was heated to reflux overnight; the reaction mixture was concentrated, and then diluted with EtOAc (30 mL). The solution was washed with saturated $NaHCO_3$, organic layer was dried over anhydrous $MgSO_4$, filtered and volatiles were removed under reduced pressure. The compound was isolated by preparative TLC to give an off-white solid 44 mg (39%). MH+ 215.9

Biological Examples

Determination of compounds HCV GT1b and GT1a entry inhibitory activity using the pseudotyped HCV particle (HCVpp) reporter assay.

Mammalian expression plasmids for the generation of pseudotyped virus particles.

Plasmids expressing HCV E1 and E2 envelope proteins of GT1a H77 strain (Proc Natl Acad Sci USA 1997 94:8738-43) or GT1b Con1 strain (Science 1999 285:110-3) were constructed by cloning the nucleic acids encoding the last 60 amino acids of HCV core protein and all of the HCV E1 and E2 proteins into pcDNA3.1(+) vector. Plasmid pVSV-G expressing the glycoprotein G of the vesicular stomatitis virus (VSV G) is from Clontech (cat #631530). The HIV packaging construct expressing the firefly luciferase reporter gene was modified based on the envelope defective pNL.4.3.Luc-R⁻.E⁻ vector (Virology 1995 206:935-44) by further deleting part of the HIV envelope protein.

Generation of pseudotyped virus particles in transiently transfected HEK-293T cells.

Pseudotyped HCV GT1a and GT1b particles (HCVpp) and the pseudotyped VSV G particles (VSVpp) were generated from transiently transfected HEK-293T cells (ATCC cat# CRL-573). For generating HCVpp, the HEK-293T cells were transfected with equal amounts of plasmids expressing the HCV envelope proteins and the HIV packaging genome by using polyethylenimine (Polysciences cat#23966) as transfection reagent. For generating VSVpp, the HEK-293T cells were transfected with equal amounts of plasmids expressing VSV G and the HIV packaging genome by using polyethylenimine. 24 hours after the transfection, the cell culture medium containing the transfection mixture was replaced with fresh Dulbecco's Modified Eagle Medium (DMEM-Glutamax™-I; Invitrogen cat #10569-010) supplemented with 10% Fetal Bovine Serum (Invitrogen cat #10082-147) and 2 mM L-glutamine (Invitrogen cat #25030-081). The supernatant was collected 48 hours after the transfection and filtered through a sterile 0.45 µm filter. Aliquots of the supernatant was frozen and stored at −80° C. until use.

Huh7-high CD81 cells with high CD81 expression level were enriched by flow cytometry sorting using FITC-labeled CD81 antibody JS-81 (BD Biosciences cat#561956) to allow more efficient HCV entry. The Huh7-high CD81 cells were cultured in Dulbecco's Modified Eagle Medium (DMEM-Glutamax™-I; Invitrogen cat #10569-010). The medium was supplemented with 10% Fetal Bovine Serum (Invitrogen cat #10082-147) and 1% penicillin/streptomycin (Invitrogen cat #15070-063). Cells were maintained at 37° C. in a humidified 5% $CO_2$ atmosphere.

Determination of compound HCVpp entry inhibitory activity in Huh7-high CD81 cells.

Huh7-high CD81 cells were plated at a cell density of 8000 cells per well in 96 well plates (Perkin Elmer, cat #6005660). Cells were plated in 100 µl of Dulbecco's Modified Eagle Medium (DMEM-Glutamax™-I, Invitrogen Cat #10569-010) supplemented with 10% Fetal Bovine Serum (Invitrogen Cat #10082-147) and 1% penicillin/streptomycin (Invitrogen cat #15070-063). Cells were allowed to equilibrate for 24 hours at 37° C. and 5% CO2 at which time compounds and pseudotyped viruses were added. On the day of the assay, HCVpp aliquots were thawed in 37° C. water bath and kept at 4° C. until use. Compounds (or medium as a control) were diluted in 3 fold dilution series in DMEM-Glutamax™-I with 2% DMSO and 2% penicillin/streptomycin. The 100 µl plating medium in each culture well was removed followed by the addition of 50 µl compound dilutions and 50 µl thawed HCVpp. Firefly luciferase reporter signal was read 72 hours after the addition of compounds and HCVpp using the Steady-Glo luciferase Assay System (Promega, cat # E2520) following the manufacturer's instruction. EC50 values were defined as the compound concentration at which a 50% reduction in the levels of firefly luciferase reporter was observed as compared to control samples in the absence of compound and was determined by non-linear fitting of compound dose-response data.

Determination of compound selectivity in Huh7-high CD81 cells.

Huh7 hCD81 cell assay plates and compound dilutions were set up in the same format as in the HCVpp assay. 24 hours after cell plating, thawed VSVpp was diluted by 800 fold in DMEM-Glutamax™-I supplemented with 10% fetal bovine serum. After removal of the cell plating medium from the culture wells, 50 µl compound dilutions and 50 µl diluted VSVpp were added to the wells. Firefly luciferase reporter signal was read 72 hours after the addition of compounds and VSVpp using the Steady-Glo luciferase Assay System (Promega, cat # E2520). EC50 values were defined as the compound concentration at which a 50% reduction in the levels of firefly luciferase reporter was observed as compared to control samples in the absence of compound and was determined by non-linear fitting of compound dose-response data. The EC50 was approximated if maximum percentage inhibition was less than 90% and more than 70%. Representative assay data can be found in Table II below:

TABLE II

| Compound # | HCVpp GT-1a ($EC_{50}$, µM) | HCVpp GT-1b ($EC_{50}$, µM) | VSVpp ($EC_{50}$, µM) |
|---|---|---|---|
| 1 | 2.764 | 48.925 | 100.0 |
| 2 | 75.428 | 100 | 100.0 |
| 3 | 0.191 | 7.076 | 100.0 |
| 4 | 100 | 100 | 100.0 |

TABLE II-continued

| Compound # | HCVpp GT-1a (EC$_{50}$, μM) | HCVpp GT-1b (EC$_{50}$, μM) | VSVpp (EC$_{50}$, μM) |
|---|---|---|---|
| 5 | 100 | | 100.0 |
| 6 | 62.207 | | 100.0 |
| 7 | 16.42 | | 100.0 |
| 8 | | 100 | 100.0 |
| 9 | | 4.714 | 100.0 |
| 10 | | 3.684 | 100.0 |
| 11 | 22.34 | | 100.0 |
| 12 | | >100 | >100.0 |

The foregoing invention has been described in some detail by way of illustration and example, for purposes of clarity and understanding. It will be obvious to one of skill in the art that changes and modifications may be practiced within the scope of the appended claims.

Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:

1. A compound of formula I:

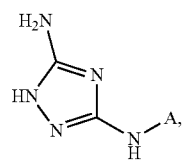

wherein:
A is an unsaturated or partially saturated bicyclic or 6-membered monocyclic heteroaryl ring, having one to three heteroatoms selected from N, O and S and the remaining ring atoms being carbon, optionally substituted with one or more A'; thiazolyl, optionally substituted with one or more A'; or thiophenyl, optionally substituted with one or more A'; and
each A' is independently halo, halo lower alkyl, lower alkyl, or oxo;
or a pharmaceutically acceptable salt thereof,
wherein said 6-membered monocyclic heteroaryl ring is selected from the group consisting of pyridyl, pyrazinyl, pyridazinyl and pyrimidinyl, optionally substituted with one or more A'; and wherein when A is pyridyl, said pyridyl is substituted with one or more halo, halo lower alkyl or oxo.

2. The compound of claim 1, wherein one A' is halo or two A' are halo.

3. The compound of claim 1, wherein A' is halo lower alkyl.

4. The compound of claim 1, wherein A' is lower alkyl.

5. The compound of claim 1, wherein A is pyridazinone, optionally substituted with one or more A'.

6. The compound of claim 1, wherein one A' is lower alkyl and the other is halo.

7. The compound of claim 1, wherein A is phthalazinone or imidazopyridinyl, optionally substituted with one or more A'.

8. A compound selected from the group consisting of:
N$^3$-(2-Chloro-pyridin-4-yl)-1H-[1,2,4]triazole-3,5-diamine;
N$^3$-(6-Trifluoromethyl-pyridin-3-yl)-1H-[1,2,4]triazole-3,5-diamine;
N$^3$-(2,6-Dichloro-pyridin-4-yl)-1H-[1,2,4]triazole-3,5-diamine;
N$^3$-(6-Trifluoromethyl-pyridin-2-yl)-1H-[1,2,4]triazole-3,5-diamine;
N$^3$-(4-tert-Butyl-thiazol-2-yl)-1H-[1,2,4]triazole-3,5-diamine;
N$^3$-(4-Trifluoromethyl-pyridin-2-yl)-1H-[1,2,4]triazole-3,5-diamine;
N$^3$-(5-Chloro-thiophen-3-yl)-1H-[1,2,4]triazole-3,5-diamine;
4-(5-Amino-1H-[1,2,4]triazol-3-ylamino)-6-chloro-2-methyl-2H-pyridazin-3-one;
6-(5-Amino-1H-[1,2,4]triazol-3-ylamino)-2H-phthalazin-1-one;
6-(5-Amino-1H-[1,2,4]triazol-3-ylamino)-2-methyl-2H-phthalazin-1-one;
N$^3$-Imidazo[1,2-a]pyridin-6-yl-1H-[1,2,4]triazole-3,5-diamine; and
N$^3$-Imidazo[1,2-a]pyridin-7-yl-1H-[1,2,4]triazole-3,5-diamine.

9. A method for treating a Hepatitis C Virus (HCV) infection comprising the step of administering to a patient in need thereof a therapeutically effective amount of a compound of claim 1.

10. A pharmaceutical composition comprising a therapeutically effective amount of a compound of claim 1 and a pharmaceutically acceptable excipient.

11. The method of claim 9, further comprising the step of administering an immune system modulator or an antiviral agent that inhibits replication of HCV, or a combination thereof.

12. The method of claim 11, wherein the immune system modulator is an interferon or a chemically derivatized interferon.

13. The method of claim 11, wherein the antiviral agent is selected from the group consisting of a HCV protease inhibitor, a HCV polymerase inhibitor, a HCV helicase inhibitor, a HCV NS5A inhibitor, or any combination thereof.

14. A pharmaceutical composition comprising a therapeutically effective amount of a compound of claim 8 and a pharmaceutically acceptable excipient.

15. A method for treating a Hepatitis C Virus (HCV) infection comprising the step of administering to a patient in need thereof a therapeutically effective amount of a compound of claim 8.

* * * * *